US012159721B1

(12) United States Patent
Makarkin et al.

(10) Patent No.: US 12,159,721 B1
(45) Date of Patent: Dec. 3, 2024

(54) SYSTEMS AND METHODS FOR PREDICTING RELATIVE PATIENT HAZARDS USING PHARMACEUTICAL ADHERENCE PREDICTIVE MODELS

(71) Applicant: Express Scripts Strategic Development, Inc., St. Louis, MO (US)

(72) Inventors: Alexi E. Makarkin, Ballwin, MO (US); Christopher G. Lehmuth, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 713 days.

(21) Appl. No.: 17/072,114

(22) Filed: Oct. 16, 2020

Related U.S. Application Data

(60) Provisional application No. 62/916,421, filed on Oct. 17, 2019.

(51) Int. Cl.
  *G16H 50/30* (2018.01)
  *G16H 20/10* (2018.01)

(52) U.S. Cl.
  CPC ............. *G16H 50/30* (2018.01); *G16H 20/10* (2018.01)

(58) Field of Classification Search
  CPC .............................. G16H 50/30; G16H 20/10
  See application file for complete search history.

(56) References Cited

U.S. PATENT DOCUMENTS

| 6,587,829 | B1 | 7/2003 | Camarda |
| 7,054,706 | B2 | 5/2006 | Kempf |
| 7,389,211 | B2 | 6/2008 | Abu El Ata |
| 7,533,038 | B2 | 5/2009 | Blume |
| 7,561,158 | B2 | 7/2009 | Abe |
| 7,565,304 | B2 | 7/2009 | Casati |
| 8,095,380 | B2 | 1/2012 | Wennberg |
| 8,666,926 | B1 | 3/2014 | Nease |
| 8,682,704 | B2 | 3/2014 | Nease, Jr. |

(Continued)

OTHER PUBLICATIONS

Krousel-Wood et al., Clinicians' Guide to Statistics for Medical Practice and Research: Part I, 2006, The Oschner Journal, vol. 6 No 2 (Year: 2006).*

(Continued)

*Primary Examiner* — Karen A Hranek
(74) *Attorney, Agent, or Firm* — Miller Johnson

(57) ABSTRACT

A modeling computing device for predicting relative patient hazards based on predicted patient pharmaceutical adherence is provided. The modeling computing device includes a processor configured to receive a set of adherence data associated with adherence to a pharmaceutical prescription by a patient. The processor is also configured to determine a set of predictive adherence scores and determine a variability score associated with the set of predictive adherence scores. The processor is further configured to integrate the set of predictive adherence scores and the variability score into a feature value. The processor is also configured to identify a hazard regression model and to apply the feature value to the hazard regression model to generate an integrated patient hazard model. The processor is also configured to process the integrated patient hazard model to determine a risk level associated with the patient, and transmit an alert based on the risk level.

24 Claims, 7 Drawing Sheets

(56) References Cited

U.S. PATENT DOCUMENTS

| | | | |
|---|---|---|---|
| 9,858,389 B2 | 1/2018 | Donovan | |
| 10,108,975 B1* | 10/2018 | Benner | G16H 40/20 |
| 10,691,776 B1* | 6/2020 | Tomala | G16H 50/30 |
| 11,429,885 B1* | 8/2022 | McNair | G16H 20/10 |
| 11,508,484 B1* | 11/2022 | Liu | A61M 16/0616 |
| 2002/0002473 A1 | 1/2002 | Schrier | |
| 2006/0085230 A1 | 4/2006 | Brill | |
| 2006/0184391 A1 | 8/2006 | Barre | |
| 2006/0289020 A1* | 12/2006 | Tabak | A61B 5/4833 702/19 |
| 2008/0109252 A1 | 5/2008 | LaFountain | |
| 2009/0177613 A1* | 7/2009 | Martinez | G16H 50/30 703/2 |
| 2010/0205008 A1 | 8/2010 | Hua | |
| 2010/0241459 A1 | 9/2010 | Rao | |
| 2011/0010328 A1* | 1/2011 | Patel | G16H 20/10 706/54 |
| 2013/0252831 A1 | 9/2013 | Chen | |
| 2013/0325498 A1 | 12/2013 | Muza, Jr. | |
| 2014/0350957 A1* | 11/2014 | Calo | G16H 10/60 705/2 |
| 2015/0032465 A1 | 1/2015 | Sundar | |
| 2015/0032598 A1 | 1/2015 | Fleming | |
| 2016/0321413 A1* | 11/2016 | Cheyne | G16H 10/60 |
| 2017/0039324 A1* | 2/2017 | Francois | G16H 10/60 |
| 2017/0116389 A1* | 4/2017 | Matlin | G16H 20/10 |
| 2017/0266813 A1* | 9/2017 | Davey | B25J 11/008 |
| 2017/0270666 A1 | 9/2017 | Barnes | |
| 2018/0113985 A1* | 4/2018 | Gandy | G16H 20/10 |
| 2019/0237201 A1 | 8/2019 | Bauman | |
| 2019/0284636 A1 | 9/2019 | Kelsey | |
| 2019/0385726 A1* | 12/2019 | Patel | G07F 9/002 |
| 2020/0020038 A1* | 1/2020 | Haile | G16H 50/30 |
| 2020/0251193 A1* | 8/2020 | White | G16B 20/20 |
| 2020/0292559 A1 | 9/2020 | Ford | |
| 2020/0321102 A1 | 10/2020 | Barnes | |
| 2020/0381095 A1* | 12/2020 | Li | G16H 50/30 |
| 2021/0151194 A1* | 5/2021 | Foschini | G16H 50/70 |
| 2021/0257073 A1* | 8/2021 | Gan | G16H 50/30 |

OTHER PUBLICATIONS

Katzman et al., DeepSurv: personalized treatment recommender system using a Cox proportional hazards deep neural network, 2018, BMC Medical Research Methodology 18:24 (Year: 2018).*

* cited by examiner

SYSTEMS AND METHODS FOR PREDICTING RELATIVE PATIENT HAZARDS USING PHARMACEUTICAL ADHERENCE PREDICTIVE MODELS

CROSS-REFERENCE TO RELATED APPLICATIONS

This application claims priority to U.S. Provisional Patent Application No. 62/916,421 filed on Oct. 17, 2019, which is incorporated by reference herein in its entirety for all purposes. This application also references U.S. Patent Application No. 2015/0032465 filed on Jul. 1, 2014, which is incorporated by reference herein in its entirety for all purposes.

FIELD OF INVENTION

The field relates to systems and methods for predicting relative hazards to patients and prospective treatment recommendations, using predictive models for prescription adherence.

BACKGROUND OF THE DISCLOSURE

Known systems and methods for predicting and identifying relative hazards to patient health rely on demographic and comorbidity data including, for example, patient health history. However, such systems and methods do not incorporate predicted patient adherence to pharmaceutical prescriptions. This data may be particularly salient for improved predictive modeling to identify relative hazards.

In the context of pharmaceutical, patient adherence quality to prescription plans can have significant ramifications. Generally, a patient may be prescribed a dosage level of a particular pharmaceutical (e.g., a number of pills, a volume of liquid drugs, or a number of inhalations of a gaseous drug) over a particular period of time. Patients may fail to adhere (i.e., fail to follow the terms of the prescription plan) for a variety of reasons including, for example, scheduling difficulties, and discomfort with taking the pharmaceutical, forgetfulness, or misplacement of the pharmaceutical. The degree to which a patient adheres to their prescription plan may impact the hazards and impacts faced by a patient. In some cases, failure to adhere to a prescription can adversely affect the health, longevity, or mortality of a patient.

Despite the significance of prescription adherence to patient health, known systems for predicting and identifying relative hazards to patient health fail to include predictive models for prescription adherence. As such, these systems are limited as they fail to incorporate a meaningful attribute that can be utilized to predict relative hazards to patient health and to improve treatments.

As such, systems and methods for predicting relative hazards to patients and prospective treatment recommendations, using predictive models for prescription adherence, are desirable.

BRIEF SUMMARY OF THE INVENTION

In one aspect, a modeling computing device for predicting relative patient hazards based on predicted patient pharmaceutical adherence is provided. The modeling computing device includes a processor and a memory. The processor is configured to receive a set of adherence data associated with adherence to a pharmaceutical prescription by a patient. The processor is also configured to determine a set of predictive adherence scores for a first time period based on the set of adherence data. The processor is additionally configured to determine a variability score associated with the set of predictive adherence scores for the first time period. The processor is further configured to integrate the set of predictive adherence scores and the variability score into a feature value. The processor is also configured to identify a hazard regression model used to predict patient hazards based on a set of predetermined risk factors. The processor is additionally configured to apply the feature value to the hazard regression model to generate an integrated patient hazard model. The processor is also configured to process the integrated patient hazard model to determine a risk level associated with the patient, and transmit an alert based on the risk level.

In another aspect, a method for predicting relative patient hazards based on predicted patient pharmaceutical adherence is provided. The method is performed by a modeling computing device including a processor and a memory. The method includes receiving a set of adherence data associated with adherence to a pharmaceutical prescription by a patient. The method also includes determining a set of predictive adherence scores for a first time period based on the set of adherence data. The method additionally includes determining a variability score associated with the set of predictive adherence scores for the first time period. Further, the method includes integrating the set of predictive adherence scores and the variability score into a feature value. The method also includes identifying a hazard regression model used to predict patient hazards based on a set of predetermined risk factors. Moreover, the method includes applying the feature value to the hazard regression model to generate an integrated patient hazard model. The method also includes processing the integrated patient hazard model to determine a risk level associated with the patient. Moreover, the method includes transmitting an alert based on the risk level.

In yet another aspect, a modeling system for predicting relative patient hazards based on predicted patient pharmaceutical adherence is provided. The modeling system includes a pharmaceutical data processing system. The pharmaceutical data processing system includes a data processor and a data memory. The modeling system also includes a modeling computing system in communication with the pharmaceutical data processing system. The modeling computing system includes a processor and a memory. The processor is configured to receive a set of adherence data from the pharmaceutical data processing system, said set of adherence data associated with adherence to a pharmaceutical prescription by a patient. The processor is also configured to determine a set of predictive adherence scores for a first time period based on the set of adherence data. The processor is additionally configured to determine a variability score associated with the set of predictive adherence scores for the first time period. The processor is further configured to integrate the set of predictive adherence scores and the variability score into a feature value. The processor is also configured to identify a hazard regression model used to predict patient hazards based on a set of predetermined risk factors. The processor is additionally configured to apply the feature value to the hazard regression model to generate an integrated patient hazard model. The processor is also configured to process the integrated patient hazard model to determine a risk level associated with the patient, and transmit an alert based on the risk level.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1:
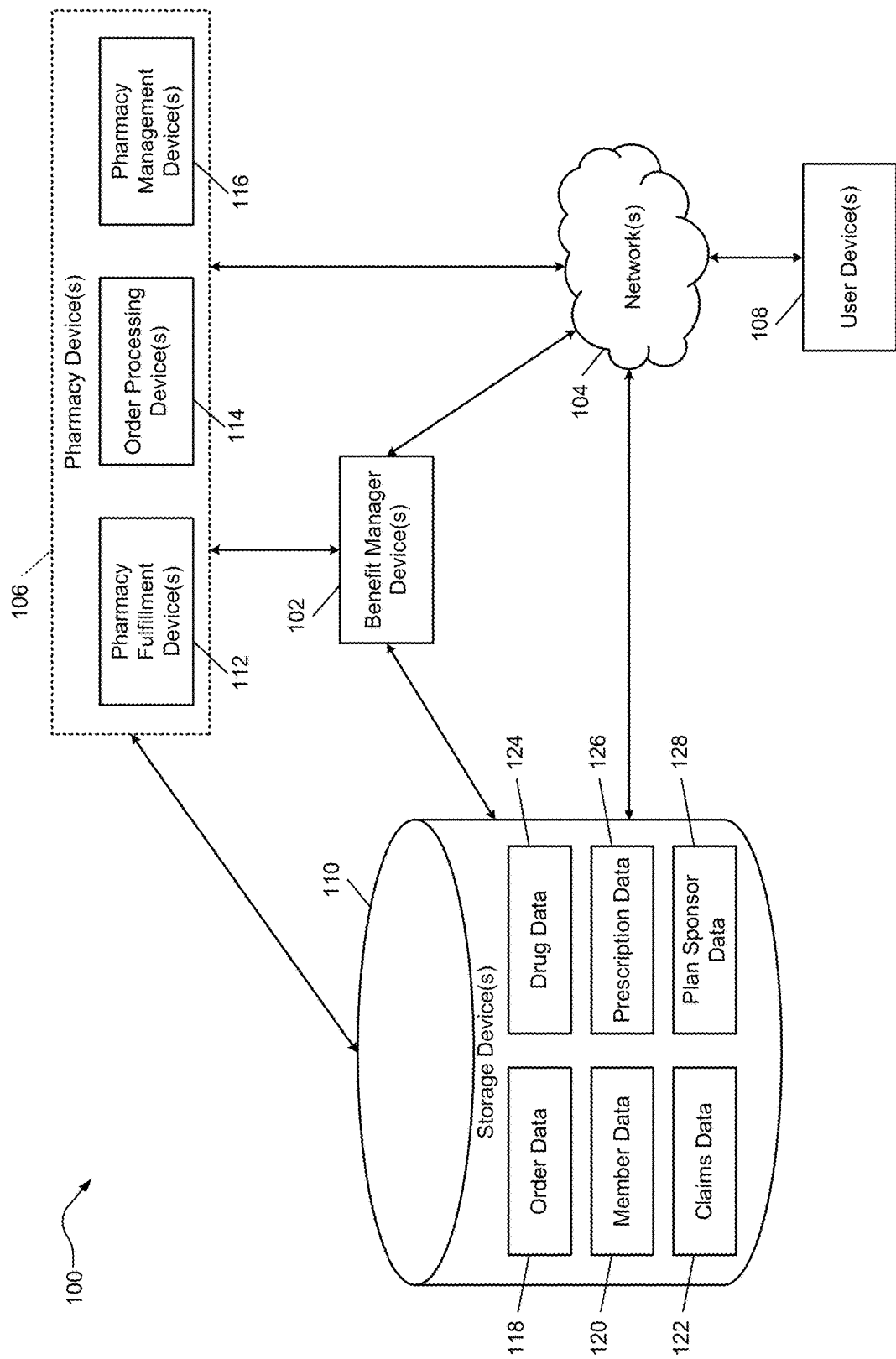
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As described above, known methods and systems for predicting and identifying patient hazards fail to incorporate predictive models related to the issue of non-adherence to prescribed medication regimens. As a result, an information gap may exist in such known methods and systems that renders them inaccurate.

The systems and methods disclosed herein address the known technological problems associated with known predictive models for patient hazards. Specifically, the present disclosure applies predictive models for patient prescription adherence to improve the quality of patient hazard predictions. The disclosure provides a technological approach of a classifier machine learning algorithm that is used to generate the patient prescription adherence predictive models. Development of the systems and methods has established a statistical link between patient prescription adherence predictive models (and their related scoring) and predictive models for patient hazards. In an example embodiment, the systems and methods apply binary logistic models to calculate predicted adherence scores and predicted relative hazards. Further, the development of the systems and methods described provides a method for quantifying the magnitude of that statistical link. The statistical link and magnitude are used to integrate the patient prescription adherence predictive models (and their related scoring) and predictive models for patient hazards.

The systems and methods described may be used on a variety of pharmaceutical prescriptions and combinations thereof including, for example, diabetes medication, cholesterol medication, metabolic drugs, respiratory drugs, neurological drugs, and any other medication for chronic or critical care. As such, the systems and methods may be used to predict and identify patient hazards for patients experiencing conditions including type I and II diabetes, hypertension, blood cholesterol, other cardiovascular disease, metabolic disease, respiratory disease, neurological disease, and other types of illness.

In the example embodiment, the methods described herein are performed by a modeling computing system in communication with a pharmaceutical data processing system. The pharmaceutical data processing system includes a data processor and a data memory. The pharmaceutical data processing system is configured to provide analytical data related to patients. In the example embodiment, the pharmaceutical data processing system provides the analytical data without any personally identifiable information (PII) and in a manner compliant with all relevant regulations including, but not limited to the Health Insurance Portability and Accountability Act (HIPAA). The pharmaceutical data processing system provides the modeling computing system with input information used to perform the predictive analytics and data modeling described herein, and thereby facilitates the patient prescription adherence predictive models and relative patient hazard predictive models described.

In the example embodiment, the analytical data is consolidated and aggregated for each patient. The analytical data includes, without restriction, age, gender, the number of prescriptions associated with the patient, flags indicating whether a patient uses particular pharmaceuticals (e.g., insulin or statin drugs), the number of chronic conditions associated with the patient, the number of acute conditions associated with the patient, a listing of the chronic conditions associated with the patient, a listing of the acute conditions associated with the patient, precursor data used to predict patient adherence to pharmaceutical prescriptions, and forecasted adherence scores grouped into multiple risk profiles. The forecasted adherence scores may be determined based on risk profiles associated with such analytical data, and based on previous scores, trends, and predictive models. The precursor data includes, but is not limited to claims data, prescription data, patient history with prescription therapy, patient disease state, patient medication possession ratio (MPR), age, income, number of medications prescribed, symptomatic diseases, partner status, and partner adherence data. In one example, the patient prescription adherence predictive models (and their related scoring) uses an approach in Appendix A, attached hereto. Appendix A describes certain approaches to adherence prediction, but these approaches may be modified for use with the methods described herein. However, in the example embodiment, the patient prescription adherence predictive model applies an algorithmic approach to calculate predictive adherence scores as a product of a classifier machine learning algorithm. In one example, the algorithmic approach applies a binary logistic model. Specifically, the algorithm transforms data from qualitative forms into a non-linear scale by applying logits and odds ratios. The algorithm applies categorical variables and/or time-varying variables to transform the data, as described below. The transformed and scaled data is weighted on a factor-by-factor basis with model weights to produce a single adherence score per patient over time. In the example embodiment, the predetermined window of time is three (3) months and the predictive adherence scores are numerical values ranging from zero (0) to one (1), where 0.0000 represents the lowest predicted adherence score indicating a patient is predicted to fail to adhere to a prescription and 1.0000 represents the highest predicted adherence score indicating a patient is predicted to fully adhere to a prescription. In another example, the predetermined window of time is twelve (12) months and the predictive adherence scores are numerical values ranging from zero (0) to one (1), where 0.0000 represents the lowest predicted adherence score indicating a patient is predicted to fail to adhere to a prescription and 1.0000 represents the highest predicted adherence score indicating a patient is predicted to fully adhere to a prescription. In this example, scores are calculated at one period of each of the twelve (12) months including, for example, the last day of each month, the first day of each month, or any fixed point in each month.

As described above, the algorithm performs data transformation using time-varying variables and/or categorical variables. Time-varying covariance occurs when a given covariate changes over time during the follow-up period. Time-varying covariates can be classified as either internal, when the path is affected by survival status, or external, when the covariate is the fixed/defined covariate. An internal covariate is typically the output of a stochastic process. An external covariate X(•), in contrast, may influence the rate of failure over time, but its path up to time t>v is not affected by the occurrence of failure time at time v. It is also a derived or predetermined covariate. The covariate allows incorporation of a time interaction function X(t) or X(g(t)).

Development of the disclosed systems and methods has revealed relationships between the analytical data and patient hazards including mortality and wellness. In some examples, the relationships may vary depending upon patient attributes such as age or gender. However, the development of the disclosed systems and methods has determined that predictive adherence scores have significantly greater relationships to patient hazards than the other analytical data. Further analysis suggests that, in the example embodiment, the predictive adherence scores are best applied to adjust the predictive model for patient hazards as follows. First, predictive adherence scores from a predetermined window of time are selected. In the example embodiment, the predetermined window of time is three (3) months and the predictive adherence scores are numerical values ranging from zero (0) to one (1). Second, the level of volatility in the predictive adherence scores for the predetermined window of time is determined and processed as a variability score. In the example embodiment, the variability score is represented by dividing a standard deviation value of the predictive adherence scores by the mean value of the predictive adherence scores. Applying this approach, a patient with a high level of predicted adherence and low level of volatility has the best prognosis according to the data. The variability score and the predictive adherence score are integrated, using a predetermined algorithm, to create a principal component that may be used to modify the predictive model for patient hazards. In the example embodiment, the predetermined algorithm is measured as a coefficient of variation (CV) based on the most recent three (3) months of predictive adherence scores for every member within a cohort population having a defined chronic or acute condition (e.g., diabetes or cardiovascular disease) or a prescribed pharmaceutical (e.g., insulin or statin drugs). In one example, the variability score may be represented in the following equation:

$$CV = \frac{\sigma}{\overline{X}}$$

where $\sigma$ is the standard deviation of the predictive adherence score for the predetermined window of time, which is three (3) months in the example embodiment; where $\overline{X}$ is the mean value of the predictive adherence score for the predetermined window of time, which is three (3) months in the example embodiment.

The modeling computing device is configured to create the principal component by identifying appropriate weights for each of the variability score and the predictive adherence score, applying such weights, and utilizing the predetermined algorithm to integrate the variability score and the predictive adherence score. In some examples, the weights are identified in part based on identified statistical relationships between the hazard regression model and the set of predictive adherence scores. In such examples, the modeling computing device is configured to identify a statistical relationship between the hazard regression model and the set of predictive adherence scores and determine the first weighting factor and the second weight factor based on the statistical relationship. Development of the disclosed systems and methods has identified that, in one example, the weighting factor for the predictive adherence score is −0.707 and the weighting factor for the variability score is 0.707. Such values may be appropriate for weighting in the context of patients with diabetes that are prescribed insulin. In other examples, other weighting factors may be determined based on the identified statistical relationship. Predictive adherence scores are typically weighted with negative values because higher predicted adherence tends to correlate with lower rates of relative patient hazards. Conversely, volatility scores are typically weighted with positive values because higher volatility scores tend to correlate with higher rates of relative patient hazards.

The principal component is used as one of the input features to capture magnitude and volatility of predicted adherence and its impact on patient hazards. In an example embodiment, the predictive model for patient hazards is a Cox proportional hazard (CPH) model. The CPH model has been identified as particularly valuable at prediction and identification of relative hazards to patients. The modeling computing device applies the principal component score (also referred to as a feature value) to the hazard regression model to generate an integrated patient hazard model. In the example embodiment, the feature value is generated, as described above, by applying weights (or loadings) to each measure (i.e., to the predictive adherence score and to the volatility score) and combining the weighted measures.

In a further embodiment, the predictive model for patient hazards is an accelerated failure time ("AFT") model. The AFT model is a parametric model that may be used as an alternative proportional hazards models such as the CPH model. Notably, while a proportional hazards model assumes that the effect of a covariate is to multiply the hazard by some constant, an AFT model assumes that the effect of a covariate is to accelerate or decelerate the life course of a disease by some constant. This is especially appealing in technical contexts where the "diseases" are a result of some mechanical process with a known sequence of intermediary stages. In one example, an AFT model may be described using the following equation: $\lambda(t|\theta)=\theta\lambda_0(\theta t)$. Notably, while parametric CPH models predict hazards, non-parametric AFT models predict survival. Thus, a positive adherence coefficient may result in a positive effect on survival and a positive AFT model score, but a negative CPH model score.

Further, all members are rank-ordered by the principal component scores (or feature values) from highest to lowest and then split into a predetermined number of groups of equal sizes. In the example embodiment, the members are split into ten (10) groups. The groups are labeled as by their respective splits in rank order. Members in the lowest ranked group (e.g., group one) have the highest predicted adherence on average and members in the highest ranked group (e.g., group ten) have the lowest predicted adherence. The groups are finally encoded into nine one-hot vectors and the highest ranked group is dropped from the inputs as a reference for the lowest adherence. The approach described was developed after training a CPH model using predictive adherence one-hot vectors and controlling for confounding factors reflected in the analytical data. This approach determined that, holding all other terms equal, higher predicted adherence tends to correlate to decreased predicted relative hazards for the patients.

The modeling computing device processes the integrated patient hazard model to determine a risk level associated with the patient. The modeling computing device is also configured to transmit an alert or a message, based on the risk level, to a suitable recipient including a healthcare provider computing device, a patient computing device, and an insurance processing system.

In some examples, this represents a determination that the patient is at an elevated risk of a hazard. In such examples, the modeling computing device is configured to identify at least one treatment recommendation based on the risk level and the integrated patient hazard model and transmit the at least one treatment recommendation to a healthcare provider.

The modeling computing device is also configured to generate an actuarial profile associated with the integrated patient hazard model. The actuarial profile identifies risks and hazards that are predicted for the patient over a prospective time period. The actuarial profile may be transmitted to a suitable recipient including, for example, an insurance processing system or a healthcare provider. The systems and methods described have been developed and tested using a data pool of nearly two million samples, with approximately 0.9% identified as deceased. The individuals identified as deceased were further associated with a time period of death, with the number of deceased individuals rising over the sample period. In one example, the model is developed for cohorts or groups of distinct age groups.

As described herein, the modeling computing device applies a classifier machine learning algorithm to a data set that is used to generate the patient prescription adherence predictive models and to predict patient hazards. Classification is the process of predicting the class of given a set of data points. Classes may also be referred to as categories, labels, or targets. Thus, classification predictive modeling is a process of approximating a mapping function from input variables to determine discrete output variables. Generally, a classifier utilizes training data to understand how given input variables relate to the class. Using the modeling computing device and the systems and methods described, the classifier machine learning algorithm therefore trains on the data pool to predict patient hazards.

In one example, the modeling computing device trains on the data using varying levels of data aggregation. Based on experimental data, predictive adherence scores that are computed quarterly have demonstrated the greatest predictive characteristics with low information loss. Thus, in at least one example, the modeling computing device trains and applies quarterly predictive adherence scores to train the predictive model and predict relative patient hazards. Further, based on experimental data, predicted adherence scores are multi-modal rather than normally distributed. (Multi-modal distributions are those probability distributions with two or more modes, or two or more "peaks".) In several examples, the modeling computing device has identified magnitude of predicted adherence and volatility of predicted adherence as salient features. As such, in some examples the modeling computing device may decompose the data sets to determine magnitude and volatility in order to determine predicted hazards. In some examples, these features may correlate such that patients with high adherence scores may have low variability in adherence over time. A principal component was created to capture these two dimensions based on adherence mean score and coefficient of variation. Patients with high principal component score tend to have consistently high adherence score over time. As such, in one example, the principal component scores are split into statistical groups (e.g., ten deciles or five quintiles) with corresponding dummy and reference groups.

The modeling computing device further analyzes covariates include some or all of: age, gender, sex, number of unique diabetes therapies, whether the patient uses insulin (e.g., as a binary value or the usage level), number of comorbidities, number of chronic comorbidities, and each principal component score group (e.g., decile) factor. Score group factors with higher adherence tend to decrease hazards to a larger degree than those with lower adherence in most examples, although some score group factors vary. The magnitude of adherence on hazards (or mortality) is not linear, which is explained by the multi-modal (non-normal) distribution of predicted adherence scores. In one experimental example, age, insulin use, and gender were determined to be the most impactful covariates. In other experimental examples, comorbidity covariates such as the number of comorbidities and/or the number of chronic comorbidities have been found by the modeling computing device to increase hazard prediction. In some experimental examples, the modeling computing device has determined that high predicted adherence is associated with lower hazard prediction. The statistical group factors may significantly impact predicted hazards. Further, in some examples, increased patient age or comorbidities may be associated with decreased impact of predicted adherence scores, due in part to the increased risk of hazards generally.

In some examples, the modeling computing device may further be trained on data sets that incorporate the cause of mortality for patients who have died. In other examples, the modeling computing device may be trained using historic predicted adherence scores (and further trained on historic actual adherence). In additional examples, other modeling approaches may be used including hypothesis testing of the proportional hazards assumption. Further, as described herein, the modeling computing device may be applied to train using a wide variety of therapeutic data involving other prescriptions, illnesses, chronic illnesses, comorbidities, and comorbidities. Therefore, the systems and methods described may be applied to a variety of therapeutic contexts. The systems and methods may further be used to provide enhanced diagnostic decisions and intervention based on the models described above and herein.

In at least one example, the systems and methods may be further extended to a use-case for healthcare provider computing devices or patient computing devices whereby users (i.e., healthcare providers or patients) may input relevant information to determine hazard scoring levels.

The modeling computing device is configured to (i) receive a set of a adherence data associated with adherence to a pharmaceutical prescription by a patient; (ii) determine a set of predictive adherence scores for a first time period based on the set of adherence data; (iii) determine a variability score associated with the set of predictive adherence scores for the first time period; (iv) integrate the set of predictive adherence scores and the variability score into a feature value; (v) identify a hazard regression model used to predict patient hazards based on a set of predetermined risk factors; (vi) apply the feature value to the hazard regression model to generate an integrated patient hazard model; (vii) process the integrated patient hazard model to determine a risk level associated with the patient; and (viii) transmit an alert based on the risk level.

Generally, the systems and methods described herein are configured to perform at least the following steps that may be performed in any order, and using any permutation of such steps: receive a set of a adherence data associated with adherence to a pharmaceutical prescription by a patient; determine a set of predictive adherence scores for a first time period based on the set of adherence data; determine a variability score associated with the set of predictive adherence scores for the first time period; integrate the set of predictive adherence scores and the variability score into a feature value; identify a hazard regression model used to predict patient hazards based on a set of predetermined risk factors; apply the feature value to the hazard regression model to generate an integrated patient hazard model; process the integrated patient hazard model to determine a risk level associated with the patient; transmit an alert based on the risk level; apply a first weighting factor to the set of predictive adherence scores; apply a second weighting factor to the variability score; utilize a first algorithm to integrate the weighted predictive adherence score and the weighted variability score; identify a statistical relationship between the hazard regression model and the set of predictive adherence scores; determine the first weighting factor and the second weight factor based on the statistical relationship; determine a standard deviation associated with the set of predictive adherence scores; determine a mean value associated with the set of predictive adherence scores; apply a second algorithm to integrate the standard deviation and the mean value to generate the variability score; identify the first time period; select the set of adherence data associated with the first time period; determine the set of predictive adherence scores by applying a classifier machine learning algorithm to the selected set of adherence data; identify at least one of a Cox proportional hazards model and an accelerated failure time model as the hazard regression model, wherein the set of predetermined risk factors includes at least one of age, gender, a numeric value of prescribed prescription drugs, a numerical value for chronic conditions, a numeric value for acute conditions, insulin use, and forecasted adherence scores grouped into multiple risk profiles; identify at least one treatment recommendation based on the risk level and the integrated patient hazard model; transmit the at least one treatment recommendation to a healthcare provider; generate an actuarial profile associated with the integrated patient hazard model; transmit the actuarial profile to an insurance processing system.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order.

The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Each of the devices 102, 104, 106, 108 and 110 may be a source of an anomaly, which can be analyzed by the anomaly analyzer and methods described herein.

Figure 2:
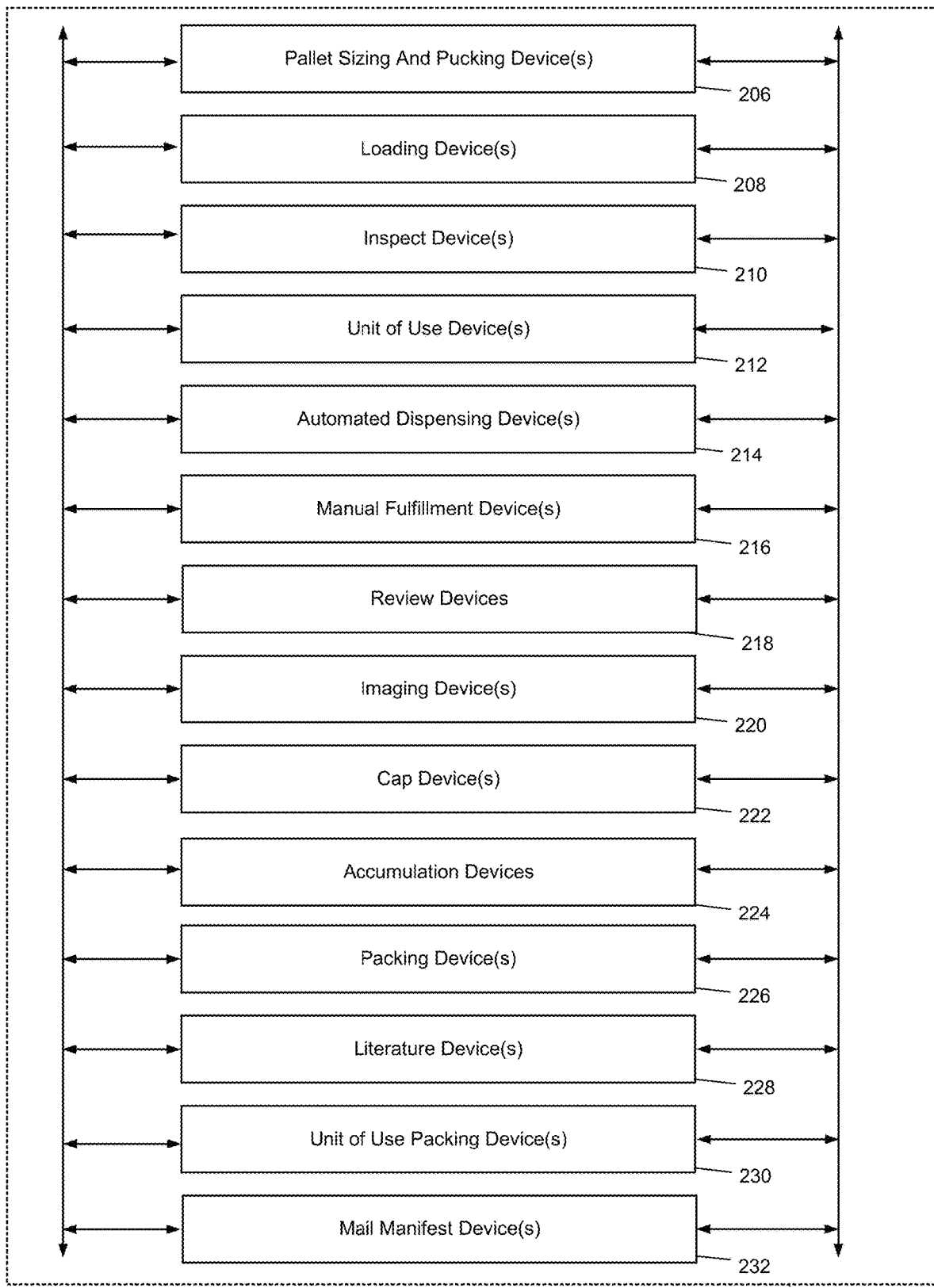
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Each of the devices in the pharmacy fulfillment device 112 may be a source of an anomaly, which can be analyzed by the anomaly analyzer and methods described herein.

Figure 3:
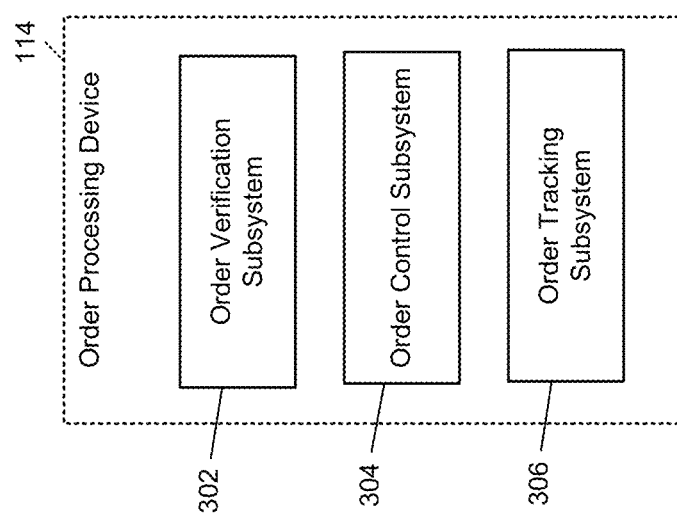
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Each of the subsystems 302, 304, or 306 in the order processing device 114 may be a source of an anomaly, which can be analyzed by the anomaly analyzer and methods described herein.

Figure 4:
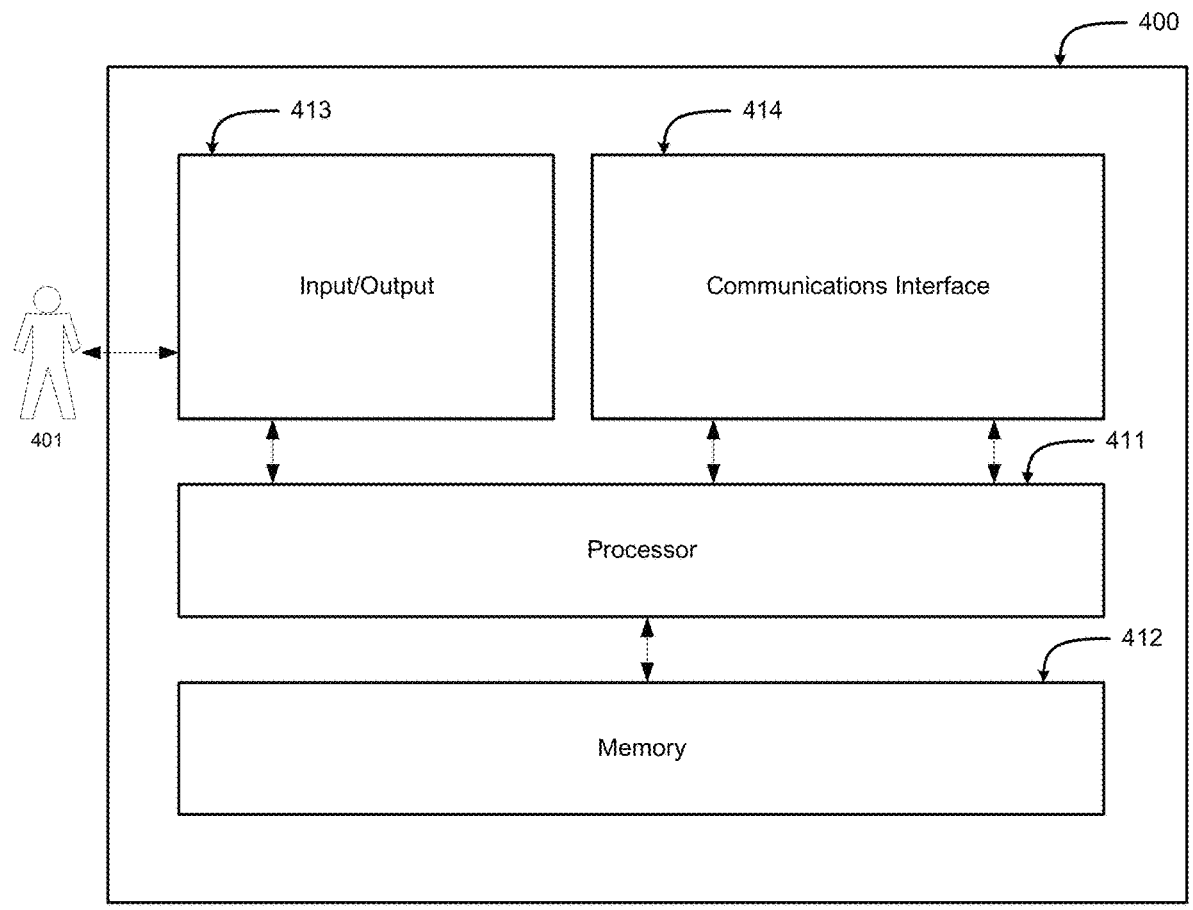
FIG. 4 is a functional block diagram of an example computing device that may be used in the environments described herein.

FIG. 4 is a functional block diagram of an example computing device 400 that may be used in the environments described herein. Specifically, computing device 400 illustrates an exemplary configuration of a computing device. Computing device 400 illustrates an exemplary configuration of a computing device operated by a user 401 in accordance with one embodiment of the present invention. Computing device 400 may include, but is not limited to, a modeling computing device, a pharmaceutical data processing system, a host device, an inventory device, and any other system described herein. Computing device 400 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 400 may be any computing device capable of predicting relative patient hazards based on predicted patient pharmaceutical adherence as described herein. In some variations, the characteristics of the described components may be more or less advanced, primitive, or non-functional.

In the exemplary embodiment, computing device 400 includes a processor 411 for executing instructions. In some embodiments, executable instructions are stored in a memory area 412. Processor 411 may include one or more processing units, for example, a multi-core configuration. Memory area 412 is any device allowing information such as executable instructions and/or written works to be stored and retrieved. Memory area 412 may include one or more computer readable media.

Computing device 400 also includes at least one input/output component 413 for receiving information from and providing information to user 401. In some examples, input/output component 413 may be of limited functionality or non-functional as in the case of some wearable computing devices. In other examples, input/output component 413 is any component capable of conveying information to or receiving information from user 401. In some embodiments, input/output component 413 includes an output adapter such as a video adapter and/or an audio adapter. Input/output component 413 may alternatively include an output device such as a display device, a liquid crystal display (LCD), organic light emitting diode (OLED) display, or "electronic ink" display, or an audio output device, a speaker or headphones. Input/output component 413 may also include any devices, modules, or structures for receiving input from user 401. Input/output component 413 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 413. Input/output component 413 may further include multiple sub-components for carrying out input and output functions.

Computing device 400 may also include a communications interface 414, which may be communicatively coupleable to a remote device such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 414 is configured to allow computing device 400 to interface with any other computing device or network using an appropriate wireless or wired communications protocol such as, without limitation, BLUETOOTH®, Ethernet, or IEE 802.11. Communications interface 414 allows computing device 400 to communicate with any other computing devices with which it is in communication or connection.

Figure 5:
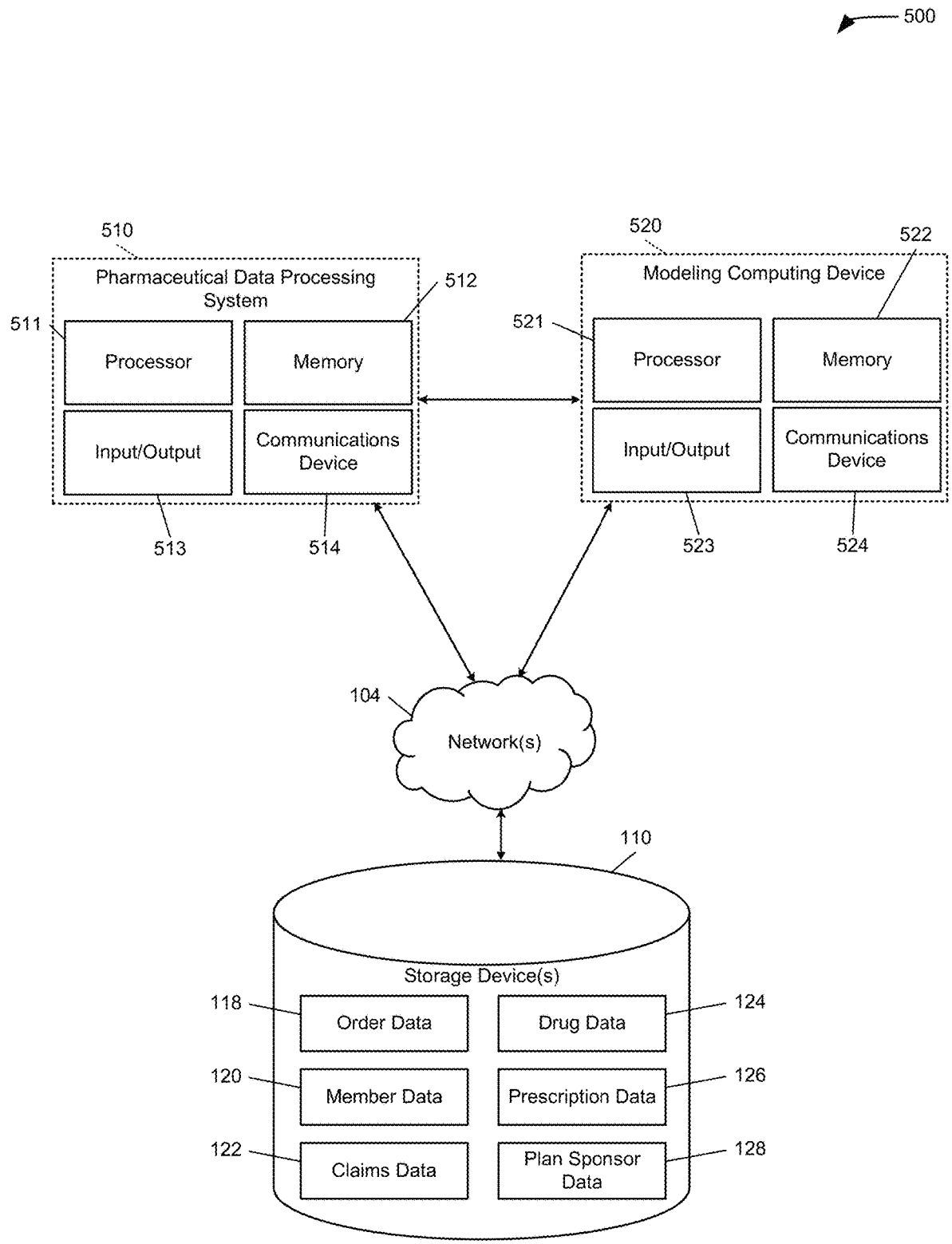
FIG. 5 is a functional block diagram of a modeling system for predicting relative patient hazards based on predicted patient pharmaceutical adherence, including a pharmaceutical data processing system and a modeling computing system, as shown in FIG. 4.

FIG. 5 is a functional block diagram of a modeling system 500 for predicting relative patient hazards based on predicted patient pharmaceutical adherence, including pharmaceutical data processing system 510 and modeling computing device 520, which are similar to the computing device 400 shown in FIG. 4. Pharmaceutical data processing system 510 includes processor 511, memory 512, input/output 513, and communications device 514. Modeling computing device 520 includes processor 521, memory 522, input/output 523, and communications device 524. Pharmaceutical data processing system 510 is in communication with modeling computing device 520. Pharmaceutical data processing system 510 and modeling computing device 520 are both in communication with network 104 and capable of accessing storage device 110. As a result, pharmaceutical data processing system 510 and modeling computing device 520 have access to analytical data available from storage device 110 including order data 118, member data 120, claims data 122, drug data 124, prescription data 126, and plan sponsor 128. In the example embodiment, pharmaceutical data processing system 510 has access to analytical data described herein through storage device 110, through memory 512, or through other devices available from network 104. Pharmaceutical data processing system 510 is configured to provide analytical data to modeling computing device 520 to facilitate the methods described herein. In at least some embodiments, pharmaceutical data processing system 510 and modeling computing device 520 are resident are one computing device that is capable of compiling and integrating analytical data along with performing the predictive analytics described.

Figure 6:
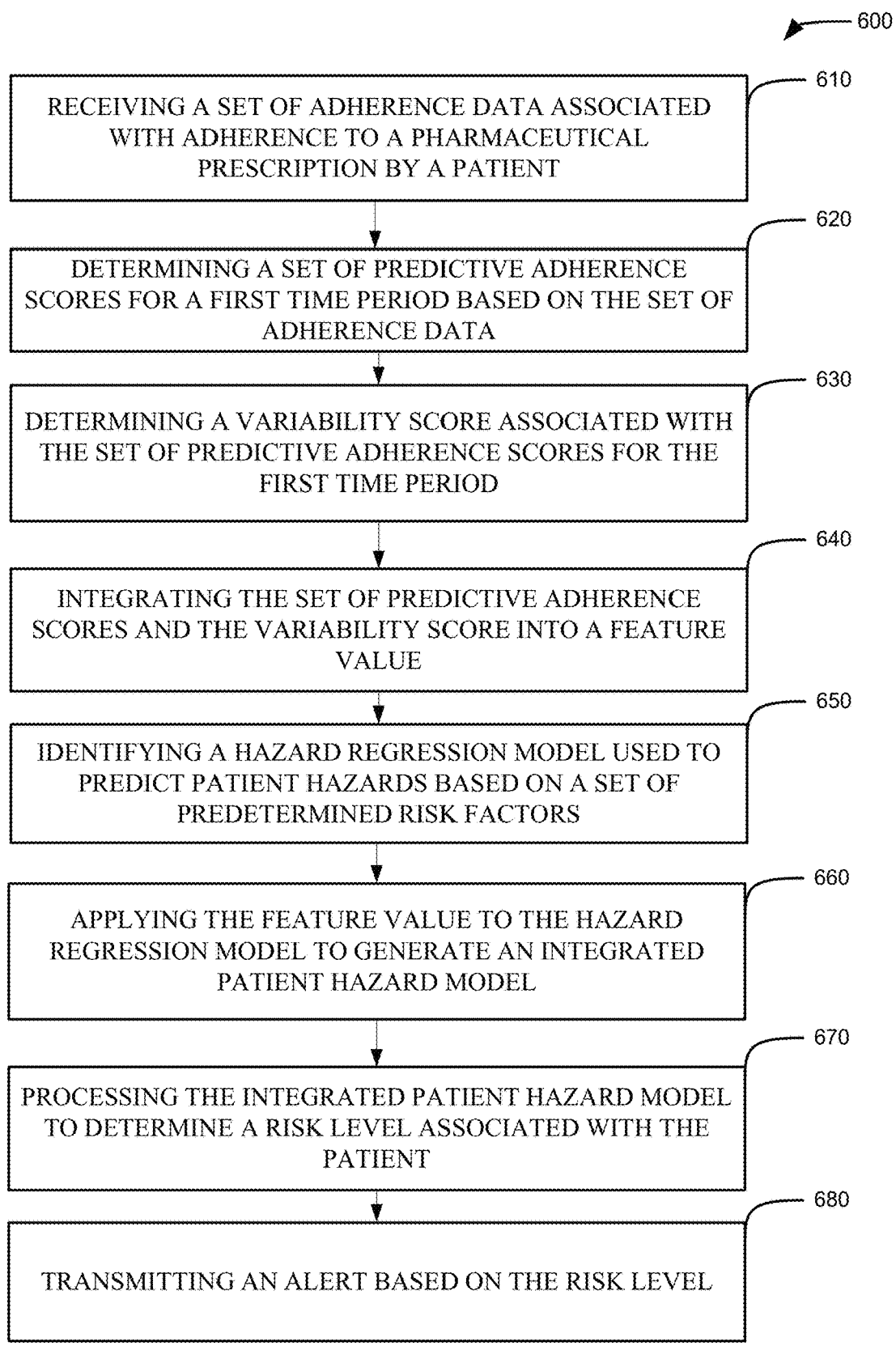
FIG. 6 is a flow diagram representing a method for predicting relative patient hazards based on predicted patient pharmaceutical adherence performed by the modeling computing device shown in FIG. 5.

FIG. 6 is a flow diagram representing a method 600 for predicting relative patient hazards based on predicted patient pharmaceutical adherence performed by the modeling computing device 520 of the modeling system 500 shown in FIG. 5. The modeling computing device 520 is configured to perform a method including receiving 610 a set of adherence data associated with adherence to a pharmaceutical prescription by a patient, determining 620 a set of predictive adherence scores for a first time period based on the set of adherence data, determining 630 a variability score associated with the set of predictive adherence scores for the first time period, integrating 640 the set of predictive adherence scores and the variability score into a feature value, identifying 650 a hazard regression model used to predict patient hazards based on a set of predetermined risk factors, applying 660 the feature value to the hazard regression model to generate an integrated patient hazard model, processing 670 the integrated patient hazard model to determine a risk level associated with the patient, and transmitting 680 an alert based on the risk level.

Figure 7:
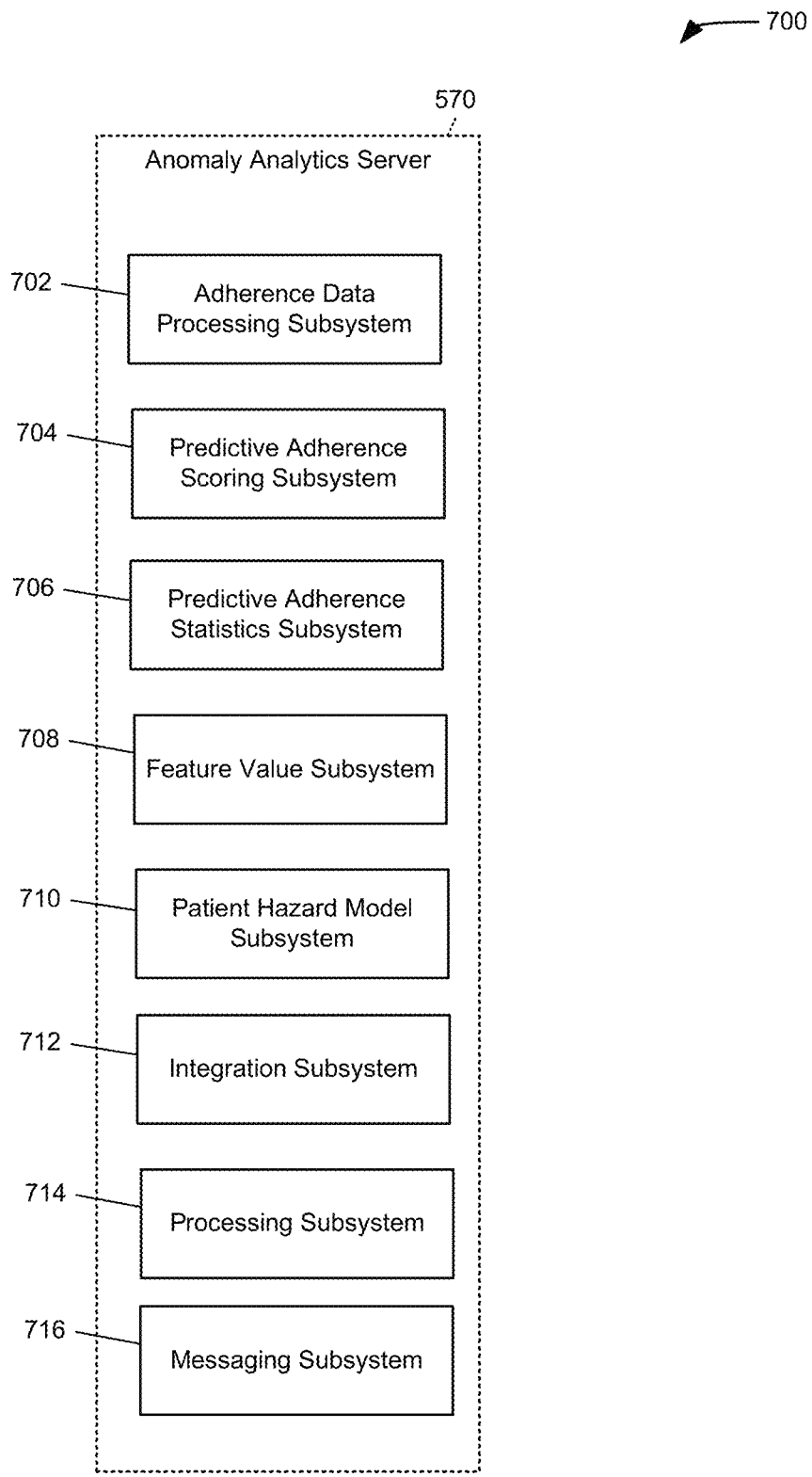
FIG. 7 is a diagram of elements of one or more example computing devices that may be used in the system shown in FIGS. 1-5.

FIG. 7 is a diagram of elements of one or more example computing devices that may be used in the system shown in FIGS. 1-5. As described herein, the elements 702, 704, 706, 708, 710, 712, 714, and 716 are configured to perform the processes and methods described herein. Adherence data processing subsystem 702 is configured to perform steps related to acquiring and processing analytical data and data used to determine predictive adherence scores. Predictive adherence scoring subsystem 704 is configured to perform steps related to predictive models for patient prescription adherence, described herein. Predictive adherence statistics subsystem 706 is configured to perform the steps of determining variability scores associated with predictive adherence scores, as described herein. Feature value subsystem 708 is configured to provide the functions of integrating the set of predictive adherence scores and the variability score into a feature value as described herein. Patient hazard model subsystem 710 is configured to identify a hazard regression model used to predict patient hazards based on a set of predetermined risk factors, according to the methods described herein. Integration subsystem 712 is configured to apply the feature value to the hazard regression model to generate an integrated patient hazard model. Processing subsystem 714 is configured to process the integrated patient hazard model to determine a risk level associated with the patient. Messaging subsystem 716 is configured to transmit an alert based on the risk level, as described herein.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A modeling computing device for predicting relative patient hazards based on predicted patient pharmaceutical adherence comprising a processor and a memory, the processor configured to:
   receive a set of historic adherence data associated with adherence to a pharmaceutical prescription by a patient;
   determine a predictive adherence score for a first time period based on the set of historic adherence data, the predictive adherence score indicating a likelihood of whether the patient will adhere to the pharmaceutical prescription over the first time period looking forward;
   determine a variability score associated with the predictive adherence score for the first time period;
   integrate the predictive adherence score and the variability score into a principal component score;
   identify a hazard regression model used to predict patient hazards based on a set of predetermined risk factors;
   apply the principal component score to the hazard regression model to generate an integrated patient hazard model configured to capture magnitude and volatility of predicted adherence and their impact on patient hazards;
   process the integrated patient hazard model to determine a risk level associated with the patient;
   identify at least one treatment recommendation based on the risk level and the integrated patient hazard model;
   fulfill, using an automated dispensing device and without operator intervention, the pharmaceutical prescription in accordance with the at least one treatment recommendation based on the risk level and the integrated patient hazard model by:
controlling movement of a set of containers relative to the automated dispensing device, and
automatically dispensing, via the automated dispensing device, the pharmaceutical prescription into a container of the set of containers; and
transmit an alert based on the risk level, the alert including the at least one treatment recommendation.

2. The modeling computing device of claim 1, wherein the processor is further configured to:
apply a first weighting factor to the predictive adherence score;
apply a second weighting factor to the variability score; and
utilize a first algorithm to integrate the weighted predictive adherence score and the weighted variability score into the principal component score.

3. The modeling computing device of claim 2, wherein the processor is further configured to:
identify a statistical relationship between the hazard regression model and the predictive adherence score; and
determine the first weighting factor and the second weighting factor based on the statistical relationship.

4. The modeling computing device of claim 1, wherein the processor is further configured to:
determine a standard deviation associated with the predictive adherence score;
determine a mean value associated with the predictive adherence score; and
apply a second algorithm to integrate the standard deviation and the mean value to generate the variability score.

5. The modeling computing device of claim 1, wherein the processor is further configured to:
identify the first time period;
select the set of historic adherence data associated with the first time period looking backward; and
determine the predictive adherence score by applying a classifier machine learning algorithm to the selected set of historic adherence data.

6. The modeling computing device of claim 1, wherein:
the processor is further configured to identify at least one of a Cox proportional hazards model or an accelerated failure time model as the hazard regression model, and
the set of predetermined risk factors includes at least one of age, gender, a numeric value of prescribed prescription drugs, a numerical value for chronic conditions, a numeric value for acute conditions, insulin use, and forecasted adherence scores grouped into multiple risk profiles.

7. The modeling computing device of claim 1, wherein the processor is further configured to transmit the at least one treatment recommendation to a healthcare provider.

8. The modeling computing device of claim 1, wherein the processor is further configured to:
generate an actuarial profile associated with the integrated patient hazard model; and
transmit the actuarial profile to an insurance processing system.

9. The modeling computing device of claim 1, wherein the processor is further configured to train the modeling computing device using a data set that incorporates a cause of mortality for patients who have died.

10. The modeling computing device of claim 1, wherein the processor is further configured to train the modeling computing device using a set of historic predicted adherence scores and the set of historic adherence data.

11. A method for predicting relative patient hazards based on predicted patient pharmaceutical adherence, the method performed by a modeling computing device including a processor and a memory, the method comprising:
receiving a set of historic adherence data associated with adherence to a pharmaceutical prescription by a patient;
determining a predictive adherence score for a first time period based on the set of historic adherence data, the predictive adherence score indicating a likelihood of whether the patient will adhere to the pharmaceutical prescription over the first time period looking forward;
determining a variability score associated with the predictive adherence score for the first time period;
integrating the predictive adherence score and the variability score into a principal component score;
identifying a hazard regression model used to predict patient hazards based on a set of predetermined risk factors;
applying the principal component score to the hazard regression model to generate an integrated patient hazard model configured to capture magnitude and volatility of predicted adherence and their impact on patient hazards;
processing the integrated patient hazard model to determine a risk level associated with the patient;
identifying at least one treatment recommendation based on the risk level and the integrated patient hazard model;
fulfilling, using an automated dispensing device configured to automatically dispense prescription drugs without operator intervention, the pharmaceutical prescription in accordance with the at least one treatment recommendation based on the risk level and the integrated patient hazard model by:
controlling movement of a set of containers relative to the automated dispensing device, and
automatically dispensing, via the automated dispensing device, the pharmaceutical prescription into a container of the set of containers; and
transmitting an alert based on the risk level, the alert including the at least one treatment recommendation.

12. The method of claim 11, further comprising:
applying a first weighting factor to the predictive adherence score;
applying a second weighting factor to the variability score; and
utilizing a first algorithm to integrate the weighted predictive adherence score and the weighted variability score into the principal component score.

13. The method of claim 12, further comprising:
identifying a statistical relationship between the hazard regression model and the predictive adherence score; and
determining the first weighting factor and the second weighting factor based on the statistical relationship.

14. The method of claim 11, further comprising:
determining a standard deviation associated with the predictive adherence score;
determining a mean value associated with the predictive adherence score; and
applying a second algorithm to integrate the standard deviation and the mean value to generate the variability score.

15. The method of claim 11, further comprising:
identifying the first time period;
selecting the set of historic adherence data associated with the first time period looking backward; and
determining the predictive adherence score by applying a classifier machine learning algorithm to the selected set of historic adherence data.

16. The method of claim 11, further comprising:
identifying at least one of a Cox proportional hazards model or an accelerated failure time model as the hazard regression model,
wherein the set of predetermined risk factors includes at least one of age, gender, a numeric value of prescribed prescription drugs, a numerical value for chronic conditions, a numeric value for acute conditions, insulin use, and forecasted adherence scores grouped into multiple risk profiles.

17. The method of claim 11, further comprising:
generating an actuarial profile associated with the integrated patient hazard model; and
transmitting the actuarial profile to an insurance processing system.

18. A modeling system for predicting relative patient hazards based on predicted patient pharmaceutical adherence, the modeling system comprising:
a pharmaceutical data processing system including a data processor and a data memory; and
a modeling computing system in communication with the pharmaceutical data processing system, the modeling computing system including a processor and a memory, the processor configured to:
receive a set of historic adherence data from the pharmaceutical data processing system, the set of historic adherence data associated with adherence to a pharmaceutical prescription by a patient;
determine a predictive adherence score for a first time period based on the set of historic adherence data, the predictive adherence score indicating a likelihood of whether the patient will adhere to the pharmaceutical prescription over the first time period looking forward;
determine a variability score associated with the predictive adherence score for the first time period;
integrate the predictive adherence score and the variability score into a principal component score;
identify a hazard regression model used to predict patient hazards based on a set of predetermined risk factors;
apply the principal component score to the hazard regression model to generate an integrated patient hazard model configured to capture magnitude and volatility of predicted adherence and their impact on patient hazards;
process the integrated patient hazard model to determine a risk level associated with the patient;
identify at least one treatment recommendation based on the risk level and the integrated patient hazard model;
fulfill, using an automated dispensing device and without operator intervention, the pharmaceutical prescription in accordance with the at least one treatment recommendation based on the risk level and the integrated patient hazard model by:
controlling movement of a set of containers relative to the automated dispensing device, and
automatically dispensing, via the automated dispensing device, the pharmaceutical prescription into a container of the set of containers; and
transmit an alert based on the risk level, the alert including the at least one treatment recommendation.

19. The modeling system of claim 18, wherein the processor is further configured to:
apply a first weighting factor to the predictive adherence score;
apply a second weighting factor to the variability score; and
apply a first algorithm to integrate the weighted predictive adherence score and the weighted variability score into the principal component score.

20. The modeling system of claim 19, wherein the processor is further configured to:
identify a statistical relationship between the hazard regression model and the predictive adherence score; and
determine the first weighting factor and the second weighting factor based on the statistical relationship.

21. The modeling system of claim 18, wherein the processor is further configured to:
determine a standard deviation associated with the predictive adherence score;
determine a mean value associated with the predictive adherence score; and
apply a second algorithm to integrate the standard deviation and the mean value to generate the variability score.

22. The modeling system of claim 18, wherein the processor is further configured to:
identify the first time period;
select the set of historic adherence data associated with the first time period looking backward; and
determine the predictive adherence score by applying a classifier machine learning algorithm to the selected set of historic adherence data.

23. The modeling system of claim 18, wherein:
the processor is further configured to identify at least one of a Cox proportional hazards model or an accelerated failure time model as the hazard regression model, and
the set of predetermined risk factors includes at least one of age, gender, a numeric value of prescribed prescription drugs, a numerical value for chronic conditions, a numeric value for acute conditions, insulin use, and forecasted adherence scores grouped into multiple risk profiles.

24. The modeling system of claim 18, wherein the processor is further configured to:
generate an actuarial profile associated with the integrated patient hazard model; and
transmit the actuarial profile to an insurance processing system.

* * * * *